United States Patent
Van Haesendonck et al.

(10) Patent No.: US 9,717,255 B2
(45) Date of Patent: Aug. 1, 2017

(54) METHOD OF PREPARING A CAKE USING PHOSPHOLIPASE

(75) Inventors: Ingrid Van Haesendonck, Mechelen (BE); Beate Andrea Kornbrust, Basel (CH)

(73) Assignee: PURATOS N.V., Groot-Bijgaarden (BE)

( * ) Notice: Subject to any disclaimer, the term of this patent is extended or adjusted under 35 U.S.C. 154(b) by 909 days.

(21) Appl. No.: 12/305,627

(22) PCT Filed: Aug. 14, 2007

(86) PCT No.: PCT/EP2007/058418
§ 371 (c)(1),
(2), (4) Date: Mar. 3, 2009

(87) PCT Pub. No.: WO2008/025674
PCT Pub. Date: Mar. 6, 2008

(65) Prior Publication Data
US 2010/0062105 A1    Mar. 11, 2010

(30) Foreign Application Priority Data
Aug. 28, 2006 (EP) .................................... 06119649

(51) Int. Cl.
*A21D 8/04* (2006.01)
*A21D 10/04* (2006.01)
*A21D 2/26* (2006.01)
*A21D 2/32* (2006.01)
*A23L 29/00* (2016.01)
*A23L 29/10* (2016.01)

(52) U.S. Cl.
CPC ............. *A21D 8/042* (2013.01); *A21D 2/261* (2013.01); *A21D 2/264* (2013.01); *A21D 2/32* (2013.01); *A23L 29/06* (2016.08); *A23L 29/10* (2016.08); *C12Y 301/01003* (2013.01); *C12Y 301/01004* (2013.01); *C12Y 301/01026* (2013.01); *C12Y 301/01032* (2013.01); *A21D 10/04* (2013.01)

(58) Field of Classification Search
CPC .......... A21D 13/08; A21D 2/32; A21D 8/042; A21D 10/04; A21D 2/261
See application file for complete search history.

(56) References Cited

U.S. PATENT DOCUMENTS

| 3,655,403 | A   | * | 4/1972  | Vidal ............................... 426/23  |
| 4,293,577 | A   | * | 10/1981 | Cillario ......................... 426/244 |
| 4,781,938 | A   | * | 11/1988 | Pflaumer et al. .............. 426/549 |
| 5,147,665 | A   | * | 9/1992  | Furcsik ........................... 426/19  |
| 6,143,545 | A   |   | 11/2000 | Clausen et al. |
| 6,235,336 | B1  |   | 5/2001  | Akashe et al. ................ 426/614 |
| 6,365,204 | B1  | * | 4/2002  | Spendler et al. .............. 426/28 |
| 6,461,649 | B1  | * | 10/2002 | Ogisu et al. .................... 426/28 |
| 6,524,631 | B1  | * | 2/2003  | Dicks .............................. 426/18 |
| 6,936,289 | B2  | * | 8/2005  | Olsen et al. ..................... 426/20 |
| 2001/0055635 | A1 |  | 12/2001 | Spendler et al. |
| 2002/0119232 | A1 | * | 8/2002 | Grazela et al. ............... 426/555 |
| 2003/0003214 | A1 | * | 1/2003 | Kraklow et al. .............. 426/551 |
| 2003/0124647 | A1 |  | 7/2003  | Sorensen et al. |
| 2003/0175383 | A1 |  | 9/2003  | Bojsen et al. |

FOREIGN PATENT DOCUMENTS

| EP | 0 426 211 A1 | 5/1991 |
| EP | 0 531 104 A2 | 9/1992 |
| EP | 0 531 104 A2 | 3/1993 |
| EP | 0 993 777 A1 | 4/2000 |
| EP | 1 145 637 A1 | 10/2001 |
| EP | 2 059 128 B1 | 7/2010 |
| JP | 63-258528 A  | 10/1988 |
| WO | WO 00/32758  | 6/2000 |
| WO | WO 2004/097012 A2 | 11/2004 |
| WO | WO 2008/025674 A1 | 3/2008 |
| WO | WO 2008/092907 A2 | 8/2008 |

OTHER PUBLICATIONS

Weihrauch et al. "The Phospholipid Content of Foods" Dec. 1983 JAOCS vol. 60 No. 12 pp. 1971-1978.*
IHS.com Jul. 2007 "Bakery Business—DSM's Cakezyme rises to the occasion" 2 pages.*
Pyler, E.J. "Baking science and technology," pp. 979-981, 1988.
International Search Report issued for corresponding PCT Application No. PCT/EP2007/058418, dated Jun. 12, 2007.
Bennion et al., The Technology of Cake Making, 6$^{th}$ Edition, Blackie Academic & Professional, New York, pp. 250-288, 1997.
Guy et al., Application of a lipase in cake manufacture, Journal of the Science of Food and Agriculture, 86:1679-1687, Aug. 30, 2006 (available online Jul. 10, 2006).
Cauvain et al., Baked Products, Science, Technology and Practice, Blackwell Publishing Ltd. Oxford, UK, pp. 57-59, 2006.
Notice of Opposition dated Dec. 20, 2010 in corresponding European Patent No. 2059128.
Response to Notice of Opposition dated Nov. 23, 2011 in corresponding European Patent No. 2059128.
Carter, T. C. (1968). The gross composition, chemistry and physico-chemical basis of organization of the yolk and white. In T. C. Carter (Ed.), *Egg Quality: A Study of the Hen's Egg* (pp. 26-58). Edinburgh: Oliver & Boyd.

(Continued)

*Primary Examiner* — Jill Warden
(74) *Attorney, Agent, or Firm* — Knobbe Martens Olson & Bear LLP

(57) ABSTRACT

The quality of a cake quality may deteriorate if the amount of eggs in the recipe is reduced. This deterioration can be counteracted by adding a phospholipase to the cake batter, as seen by an increased cake volume and improved cake properties after storage, e.g. increased cohesiveness, increased springiness, and increased elasticity. The cake quality (as measured by these parameters) can be further improved, even up to the level of the original cake, by adding a non-egg protein together with the phospholipase. Accordingly, a cake is prepared by a method, comprising: a) preparing a cake batter by mixing cake batter ingredients, said ingredients comprising non-phospholipase treated egg lecithin and phospholipase, and b) baking the cake batter to make the cake.

19 Claims, No Drawings

(56) References Cited

OTHER PUBLICATIONS

Conforti, et al. 1998. Effect of Commercial Enzymes on the Baking and Keeping Quality of a Fat Reduced Muffin. *Journal of Food Quality*, 21:85-94.
Conforti, F. D. (2006). Bakery Products: Science and Technology. In Hui, Y. H. (Ed.), *Cake Manufacture* (Chap. 22, pp. 393-410). Ames, IA: Blackwell.
Cross, N. (2006). Bakery Products: Science and Technology. In Hui, Y. H. (Ed.), *Muffins and Bagels* (Chap. 28, pp. 497-518). Ames, IA: Blackwell.
Delcour, J. A., & Hoseney, R. C. (2010). Principles of Cereal Science and Technology. *Rheology of Doughs and Batters* (Chap. 5, pp. 87-96.). St. Paul: AACC International.
Priority document EP 06119649.9 filed Aug. 28, 2006, for International Application No. PCT/EP2007/058418 filed Aug. 17, 2007, published on Mar. 6, 2008 as WO 2008/025674. Opposition Proceedings in European Application No. 07802604.4. Cited during the opposition procedure, Document D0c.
Priority document EP 07101567.1 filed Feb. 1, 2007, for International Application No. PCT/EP2008/051147 filed Jan. 30, 2008, published on Aug. 7, 2008 as WO 2008/092907 A2. Opposition Proceedings in European Application No. 07802604.4. Cited during the opposition procedure, Document D6b.
Priority document EP 07112741.9 filed Jul. 19, 2007, for International Application No. PCT/EP2008/051147 filed Jan. 30, 2008, published on Aug. 7, 2008 as WO 2008/092907 A2. Opposition Proceedings in European Application No. 07802604.4. Cited during the opposition procedure, Document D6c.
GRAS Notification of phospholipase $A_2$ from a genetically modified strain if *Aspergillus niger*, Oct. 2005, http://www.accessdata.fda.gov/scripts/fcn/gras_notices/grn000183.pdf, 130 pages. Bates No. 000001-000155. Opposition Proceedings in European Application No. 07802604.4. Cited during the opposition procedure, Document D9a.
Committee on Food Chemicals Codex. Jul. 1, 1996. Phospholiphase A2 activity. *Food Chemicals Codex*, 4th Ed. p. 808. Washington, DC: National Academy Press. Opposition Proceedings in European Application No. 07802604.4. Cited during the opposition procedure in Document D9a.
Schuster, et al. 2002. On the safety of *Aspergillus niger*—A review. *Applied Microbiology and Biotechnology*, 59:426-435. Opposition Proceedings in European Application No. 07802604.4. Cited during the opposition procedure in Document D9a.
The 31st Meeting of the Joint FAO/WHO Expert Committee on Food Additives. Feb. 1987. *Enzymes derived from Aspergillus niger: General comments on enzymes from A. niger*, 9 pages. Retrieved on Apr. 10, 2014, from http://www.inchem.org/documents/jecfa/jecmono/v22je04.htm. Opposition Proceedings in European Application No. 07802604.4. Cited during the opposition procedure in Document D9a.
Van Dijck, et al. 2003. On the safety of a new generation of DSM *Aspergillus niger* enzyme productions strains. *Regulatory Toxicology and Pharmacology*, 38:27-35. Opposition Proceedings in European Application No. 07802604.4. Cited during the opposition procedure in Document D9a.
World Health Organization, Joint FAO/WHO Expert Committee on Food Additives. 1990. Evaluation of certain food additives and contaminants: Thirty-fifth Report of the Joint FAO/WHO Expert Committee on Food Additives, 48 pages. World Health Organization Technical Report Series 789. Geneva. Cited pp. 15, 44-46 during the opposition procedure in Document D9a.
U.S. Food and Drug Administration, Center for Food Safety and Applied Nutrition / Office of Food Additive Safety, Summary of All GRAS Notices, Aug. 14, 2006, 14 pages. http://web.archive.org/web/20060820101641/http://www.cfsan.fda.gov/~rdb/opa-gras.html. Opposition Proceedings in European Application No. 07802604.4. Cited during the opposition procedure, Document D9b.
U.S. Food and Drug Administration, Center for Food Safety and Applied Nutrition / Office of Food Additive Safety, Agency Response Letter GRAS Notice No. GRN 000183, May 11, 2006, 4 pages. http://web.archive.org/web/20060926113958/www.cfsan.fda.gov/~rdb/opa-g183.html. Opposition Proceedings in European Application No. 07802604.4. Cited during the opposition procedure, Document D9c.
Guy, et al. Aug. 30, 2006. Application of a lipase in cake manufacture. *Journal of the Sicence of Food and Agriculture*, 86:1679-1687. Published online Jul. 10, 2006. Opposition Proceedings in European Application No. 07802604.4. Cited during the opposition procedure, Document D10a.
Society of Chemical Industry. Internet Table of contents of *Journal of the Science of Food and Agriculture*, 86(11), 5 pages. Retrieved on Dec. 7, 2010, from http://www3.interscience.wiley.com/journal/112729569/issue. Opposition Proceedings in European Application No. 07802604.4. Cited during the opposition procedure, Document D10b.
Presentation: Unlimited opportunities for new product development in the cake industry given by José Mastenbroek (DSM) at the IFT Food Expo 2007, 12 pages. Chicago, USA. Jul. 29, 2007. Opposition Proceedings in European Application No. 07802604.4. Cited during the opposition procedure, Document D11a.
Declaration of José Mastenbroek. 1 page. Opposition Proceedings in European Application No. 07802604.4. Cited during the opposition procedure, Document D11b.
*Curriculum vitae* of José Mastenbroek. 4 pages. Opposition Proceedings in European Application No. 07802604.4. Cited during the opposition procedure, Document D11c.
Cauvain, S. P., and Young, L. S. 2006. *Baked Products: Science, Technology and Practice* (pp. 57, 59), 4 pages. Oxford: Blackwell Publishing. Opposition Proceedings in European Application No. 07802604.4. Cited during the opposition procedure, Document D12.
Watkins, B. A. 1995. The nutritive value of the egg. In Stadelman, W. J., and O. J. Cotterill (Eds.), *Egg Science and Technology*, 4th Ed, Chap. 7 (pp. 177-194). New York: Food Products Press. Opposition Proceedings in European Application No. 07802604.4. Cited during the opposition procedure, Document D14.
Bennion, E. B., and Bamford, G. S. T. 1997. Chap. 21: Cake-making process; Chap. 22: Sponge goods; Chap. 23: Almond goods. In A. J. Bent (Ed.), *The Technology of Cake Making*, 6th Ed, (pp. 251-288). London: Balckie Academic & Professional, Chapmann & Hall. Opposition Proceedings in European Application No. 07802604.4. Cited during the opposition procedure, Document D17.
Product data sheet of Prolite—functional wheat proteins, 2 pages. Opposition Proceedings in European Application No. 07802604.4. Cited during the opposition procedure, Document D19.
PROBIOTA. Feb. 9, 2007. ADM launches functional wheat protein isolates. Retrieved Jan. 12, 2014, from http://www.nutraingredients-usa.com/Suppliers2/ADM-launches-functional-wheat-protein-isolates, 4 pages. Opposition Proceedings in European Application No. 07802604.4. Cited during the opposition procedure, Document D19a.
Test of egg replacement solution in recipe from Document D12, 7 pages. Opposition Proceedings in European Application No. 07802604.4. Cited during the opposition procedure, Document D20.
Lecithin content in whole eggs and egg powder, 1 page. Opposition Proceedings in European Application No. 07802604.4. Cited during the opposition procedure, Document D21.
Cauvain, S. P., and Young, L. S. 2006. Ingredients and their influences. *Baked Products: Science, Technology and Practice* (p. 93). Oxford: Blackwell Publishing. Opposition Proceedings in European Application No. 07802604.4. Cited during the opposition procedure, Document D22.
Opposition Proceedings in European Application No. 07802604.4. Apr. 8, 2014. EPO Form 2701, 2 pages.
Opposition Proceedings in European Application No. 07802604.4. Apr. 4, 2014. Potter Clarkson executed acknowledgment of receipt of Notice, 1 page.

(56) References Cited

OTHER PUBLICATIONS

Opposition Proceedings in European Application No. 07802604.4. Apr. 3, 2014. Potter Clarkson executed acknowledgment of receipt of Notice, 2 pages.
Opposition Proceedings in European Application No. 07802604.4. Apr. 2, 2014. DSM Intellectual Property executed acknowledgment of receipt of Notice, 1 page.
Opposition Proceedings in European Application No. 07802604.4. European Patent Office request dated Mar. 28, 2014 to Potter Clarkson LLP for acknowledgment of receipt of Notice, 1 page.
Opposition Proceedings in European Application No. 07802604.4. European Patent Office request dated Mar. 28, 2014 to DSM Intellectual Property for acknowledgment of receipt of Notice, 1 page.
Opposition Proceedings in European Application No. 07802604.4. Mar. 28, 2014. Decision in Opposition Proceedings, Annex to the Communication—Opposition, 2 pages.
Opposition Proceedings in European Application No. 07802604.4. Decision in Opposition Proceedings, Mar. 28, 2014. Interlocutory decision in oppostion proceedings (Art. 101(3)(a) and 106(2) EPC), 1 page.
Opposition Proceedings in European Application No. 07802604.4. Mar. 28, 2014. Decision in Opposition Proceedings, Druckexemplar in Opposition Procedure, 12 pages.
Opposition Proceedings in European Application No. 07802604.4. Mar. 28, 2014. Decision in Opposition Proceedings, Grounds for the Decision (Annex)—Opposition, Facts and submissions, Reasons for the decision, 6 pages.
Opposition Proceedings in European Application No. 07802604.4. Mar. 28, 2014. Decision in Opposition Proceedings, Interlocutory Decision in Opposition proceedings (Art. 101(3)(a) and 106(2) EPC), 2 pages.
Opposition Proceedings in European Application No. 07802604.4. Mar. 28, 2014. Decision in Opposition Proceedings, Internal Forms—Opposition Addresses, 2 pages.
Opposition Proceedings in European Application No. 07802604.4. Mar. 28, 2014. Decision in Opposition Proceedings, Minutes of the Oral Proceedings (Opposition Division)—Conclusion of the Proceedings, 2 pages.
Opposition Proceedings in European Application No. 07802604.4. Mar. 28, 2014. Decision in Opposition Proceedings, Minutes of the Oral Proceedings (Opposition Division)—Introduction of the Parties, 1 page.
Opposition Proceedings in European Application No. 07802604.4. Mar. 28, 2014. Provision of the Minutes with Citation Sheet, Main Request, Auxiliary Request 1, and Annexes 1-3, 14 pages.
Opposition Proceedings in European Application No. 07802604.4. Mar. 24, 2014. Notice of Appeal, 1 page.
Opposition Proceedings in European Application No. 07802604.4. Mar. 20, 2014. Notice of Appeal, 2 pages.
Opposition Proceedings in European Application No. 07802604.4. Feb. 19, 2014. Information about the result of oral proceedings, EPO Form 2341, 1 page.
Opposition Proceedings in European Application No. 07802604.4. Feb. 17, 2014. Revised Auxiliary Request 11 during Opposition procedure, 1 page.
Opposition Proceedings in European Application No. 07802604.4. Feb. 17, 2014. Revised Auxiliary Request 10 during Opposition procedure, 1 page.
Opposition Proceedings in European Application No. 07802604.4. Feb. 17, 2014. Written submission in preparation to/during oral proceeding enclosing new versions of Auxiliary Requests 10 and 11, 1 page.
Opposition Proceedings in European Application No. 07802604.4. Feb. 14, 2014. Auxiliary Request 10 during Opposition procedure, 1 page.
Opposition Proceedings in European Application No. 07802604.4. Feb. 14, 2014. Auxiliary Request 11 during Opposition procedure, 1 page.
Opposition Proceedings in European Application No. 07802604.4. Feb. 14, 2014. Faxed written submission in preparation to/during oral proceedings enclosing new versions of Auxiliary Requests 10 and 11 during Opposition procedure, 2 pages.
Opposition Proceedings in European Application No. 07802604.4. Feb. 13, 2014. Electronic Receipt of online submission, 2 pages.
Opposition Proceedings in European Application No. 07802604.4. Feb. 13, 2014. Any annexes (other than citation) to an opposition letter, Annex 2, 1 page.
Opposition Proceedings in European Application No. 07802604.4. Feb. 13, 2014. Any annexes (other than citation) to an opposition letter, Annex 1, 1 page.
Opposition Proceedings in European Application No. 07802604.4. Feb. 13, 2014. Any annexes (other than citation) to an opposition letter, Annex 3, 1 page.
Opposition Proceedings in European Application No. 07802604.4. Feb. 13, 2014. Any annexes (other than citation) to an opposition letter, Annex 4, 1 page.
Opposition Proceedings in European Application No. 07802604.4. Feb. 13, 2014. Letter accompanying subsequently filed items, 2 pages.
Opposition Proceedings in European Application No. 07802604.4. Feb. 13, 2014. Written submission in preparation to/during oral proceedings, 16 pages.
Opposition Proceedings in European Application No. 07802604.4. Feb. 5, 2014. Brief EPO communication enclosing Letter from proprietor of patent of Jan. 30, 2014, 1 page.
Opposition Proceedings in European Application No. 07802604.4. Jan. 31, 2014. Claims, Auxiliary Request 11, 1 page.
Opposition Proceedings in European Application No. 07802604.4. Jan. 31, 2014. Claims, Auxiliary Request 10, 1 page.
Opposition Proceedings in European Application No. 07802604.4. Jan. 31, 2014. Claims, Auxiliary Request 10, marked-up version, 1 page.
Opposition Proceedings in European Application No. 07802604.4. Jan. 31, 2014. Claims, Auxiliary Request 11, marked-up version, 1 page.
Opposition Proceedings in European Application No. 07802604.4. Jan. 31, 2014. Confirmation Potter Clarkson letter regarding the opposition procedure (no time limit), 2 pages.
Opposition Proceedings in European Application No. 07802604.4. Jan. 30, 2014. Auxiliary Request 11 during Opposition procedure, tracked version compared to Auxiliary Request 1, 1 page.
Opposition Proceedings in European Application No. 07802604.4. Jan. 30, 2014. Auxiliary Request 10 during Opposition procedure, clean version compared to Auxiliary Request 1, 1 page.
Opposition Proceedings in European Application No. 07802604.4. Jan. 30, 2014. Auxiliary Request 11 during Opposition procedure, clean version compared to Auxiliary Request 1, 1 page.
Opposition Proceedings in European Application No. 07802604.4. Jan. 30, 2014. Auxiliary Request 10 during Opposition procedure, tracked version compared to Auxiliary Request 1, 1 page.
Opposition Proceedings in European Application No. 07802604.4. Jan. 30, 2014. Fax cover sheet regarding the opposition procedure (no time limit), 1 page.
Opposition Proceedings in European Application No. 07802604.4. Jan. 30, 2014. Potter Clarkson written submission in preparation to/during oral proceedings, 2 pages.
Opposition Proceedings in European Application No. 07802604.4. Jan. 24, 2014. Brief EPO communication enclosing letter of Jan. 17, 2014 from opponent—Opposition proceedings, 1 page.
Opposition Proceedings in European Application No. 07802604.4. Jan. 24, 2014. Brief EPO communication enclosing letter of Jan. 16, 2014 and confirmation of Jan. 17, 2014 from proprietor of patent—Opposition proceedings, 1 page.
Opposition Proceedings in European Application No. 07802604.4. Jan. 17, 2014. (Electronic) Receipt of online submission, 2 pages.
Opposition Proceedings in European Application No. 07802604.4. Jan. 17, 2014. Any annexes (other than citation) to an opposition letter, Curriculum Vitae of Henrik Østdal, 4 pages.
Opposition Proceedings in European Application No. 07802604.4. Jan. 17, 2014. Claims, Auxixliary Request 3, 1 page.

(56) References Cited

OTHER PUBLICATIONS

Opposition Proceedings in European Application No. 07802604.4. Jan. 17, 2014. Claims, Auxiliary Request 7, 1 page.
Opposition Proceedings in European Application No. 07802604.4. Jan. 17, 2014. Claims, Auxiliary Request 5, 1 page.
Opposition Proceedings in European Application No. 07802604.4. Jan. 17, 2014. Claims, Auxiliary Request 6, 1 page.
Opposition Proceedings in European Application No. 07802604.4. Jan. 17, 2014. Claims, Auxiliary Request 2, 1 page.
Opposition Proceedings in European Application No. 07802604.4. Jan. 17, 2014. Claims, Auxiliary Request 9, 1 page.
Opposition Proceedings in European Application No. 07802604.4. Jan. 17, 2014. Claims, Auxiliary Request 1, 1 page.
Opposition Proceedings in European Application No. 07802604.4. Jan. 17, 2014. Claims, Auxiliary Request 4, 1 page.
Opposition Proceedings in European Application No. 07802604.4. Jan. 17, 2014. Claims, Auxiliary Request 8, 1 page.
Opposition Proceedings in European Application No. 07802604.4. Jan. 17, 2014. Letter accompanying subsequently filed items, DSM submission in opposition proceedings made following summons to attend oral proceedings, 2 pages.
Opposition Proceedings in European Application No. 07802604.4. Jan. 17, 2014. Potter Clarkson letter regarding the opposition procedure (no time limit), 4 pages.
Opposition Proceedings in European Application No. 07802604.4. Jan. 17, 2014. Non-scannable object, EPO black-and-white non-patent literature submitted by Potter Clarkson as D20, 7 pages.
Opposition Proceedings in European Application No. 07802604.4. Jan. 17, 2014. Non-scannable object, EPO notation that black-and-white copy made of colored document submitted by Potter Clarkson as D20, 1 page.
Opposition Proceedings in European Application No. 07802604.4. Jan. 17, 2014. DSM written submission in preparation to/during oral proceedings, 12 pages.
Opposition Proceedings in European Application No. 07802604.4. Jan. 16, 2014. Any annexes (other than citation) to an opposition letter, faxed copy of Curriculum Vitae of Henrik Østdal, 4 pages.
Opposition Proceedings in European Application No. 07802604.4. Jan. 16, 2014. Auxiliary request during Opposition procedure, faxed copy of Auxiliary Request 2, 1 page.
Opposition Proceedings in European Application No. 07802604.4. Jan. 16, 2014. Auxiliary request during Opposition procedure, faxed copy of Auxiliary Request 4, 1 page.
Opposition Proceedings in European Application No. 07802604.4. Jan. 16, 2014. Auxiliary request during Opposition procedure, faxed copy of Auxiliary Request 5, 1 page.
Opposition Proceedings in European Application No. 07802604.4. Jan. 16, 2014. Auxiliary request during Opposition procedure, faxed copy of Auxiliary Request 8, 1 page.
Opposition Proceedings in European Application No. 07802604.4. Jan. 16, 2014. Auxiliary request during Opposition procedure, faxed copy of Auxiliary Request 6, 1 page.
Opposition Proceedings in European Application No. 07802604.4. Jan. 16, 2014. Auxiliary request during Opposition procedure, faxed copy of Auxiliary Request 3, 1 page.
Opposition Proceedings in European Application No. 07802604.4. Jan. 16, 2014. Auxiliary request during Opposition procedure, faxed copy of Auxiliary Request 9, 1 page.
Opposition Proceedings in European Application No. 07802604.4. Jan. 16, 2014. Auxiliary request during Opposition procedure, faxed copy of Auxiliary Request 1, 1 page.
Opposition Proceedings in European Application No. 07802604.4. Jan. 16, 2014. Auxiliary request during Opposition procedure, faxed copy of Auxiliary Request 7, 1 page.
Opposition Proceedings in European Application No. 07802604.4. Jan. 16, 2014. Letter regarding the opposition procedure (no time limit), fax cover sheet, 1 page.
Opposition Proceedings in European Application No. 07802604.4. Jan. 16, 2014. Fax of Potter Clarkson written submission in preparation to/during oral proceedings, 4 pages.
Opposition Proceedings in European Application No. 07802604.4. Jan. 2, 2014. EPO Brief communication enclosing letter from opponent of Dec. 16, 2013, 1 page.
Opposition Proceedings in European Application No. 07802604.4. Dec. 16, 2013. (Electronic) Receipt of online submission, 1 page.
Opposition Proceedings in European Application No. 07802604.4. Dec. 16, 2013. DSM Request for interpreters during oral proceedings, 1 page.
Opposition Proceedings in European Application No. 07802604.4. Dec. 16, 2013. Written submission in preparation to/during oral proceedings, 1 page.
Opposition Proceedings in European Application No. 07802604.4. Nov. 18, 2013. DSM executed acknowledgment of delivery, 2 pages.
Opposition Proceedings in European Application No. 07802604.4. Nov. 12, 2013. EPO Brief communication enclosing letter from proprietor of patent of Nov. 4, 2013, 1 page.
Opposition Proceedings in European Application No. 07802604.4. Nov. 5, 2013. EPO receipt of Request for interpreters during oral proceedings, 1 page.
Opposition Proceedings in European Application No. 07802604.4. Oct. 30, 2013. Fax copy of Potter Clarkson executed acknowledgment of receipt of delivery, 1 page.
Opposition Proceedings in European Application No. 07802604.4. Oct. 30, 2013. Potter Clarkson executed acknowledgment of delivery, 2 pages.
Opposition Proceedings in European Application No. 07802604.4. Oct. 30, 2013. DSM executed acknowledgment of delivery, 1 page.
Opposition Proceedings in European Application No. 07802604.4. Oct. 23, 2013. EPO request for Acknowledgement of a document, 1 page.
Opposition Proceedings in European Application No. 07802604.4. Oct. 23, 2013. Annex to a communication, Annex 1, Citation Sheet, 1 page.
Opposition Proceedings in European Application No. 07802604.4. Oct. 23, 2013. Annex to the communication—opposition, 4 pages.
Opposition Proceedings in European Application No. 07802604.4. Oct. 23, 2013. Summons to DSM to attend oral proceedings, 1 page.
Opposition Proceedings in European Application No. 07802604.4. Oct. 23, 2013. Summons to Potter Clarkson to attend oral proceedings, 1 page.
Opposition Proceedings in European Application No. 07802604.4. Oct. 16, 2013. Information about the result of oral proceedings, 1 page.
Opposition Proceedings in European Application No. 07802604.4. Oct. 16, 2013. Information concerning oral proceedings, 3 pages.
Opposition Proceedings in European Application No. 07802604.4. Oct. 16, 2013. Preparation for oral proceedings, 2 pages.
Opposition Proceedings in European Application No. 07802604.4. Sep. 23, 2013. Request for change of opponent's representative, 1 page.
Opposition Proceedings in European Application No. 07802604.4. Aug. 8, 2013. Communication of amended entries concerning the representative, 1 page.
Opposition Proceedings in European Application No. 07802604.4. Aug. 2, 2013. Confirmation request for change of applicant's representative, 1 page.
Opposition Proceedings in European Application No. 07802604.4. Jul. 31, 2013. Faxed request for change of applicant's representative, 1 page.
Opposition Proceedings in European Application No. 07802604.4. Mar. 20, 2013. Brief EPO communication enclosing EPO Form 2548 of Mar. 20, 2013, 2 pages.
Opposition Proceedings in European Application No. 07802604.4. Mar. 20, 2013. Communication of amended entries concerning the representative, EPO Form 2548, 1 page.
Opposition Proceedings in European Application No. 07802604.4. Jan. 21, 2013. Confirmation letter regarding representative's new address, 1 page.
Opposition Proceedings in European Application No. 07802604.4. Jan. 16, 2013. Cover sheet for fax transmission of letter regarding representative's new address, 1 page.

(56) References Cited

OTHER PUBLICATIONS

Opposition Proceedings in European Application No. 07802604.4. Jan. 16, 2013. Faxed letter regarding representative's new address, 1 page.
Opposition Proceedings in European Application No. 07802604.4. Jan. 14, 2013. Brief EPO communication enclosing letters from opponent of Dec. 19, 2012 and Jan. 9, 2013, 1 page.
Opposition Proceedings in European Application No. 07802604.4. Jan. 10, 2013. Communication of amended entries concerning the representative, 1 page.
Opposition Proceedings in European Application No. 07802604.4. Jan. 9, 2013. (Electronic) Receipt of online submission, 1 page.
Opposition Proceedings in European Application No. 07802604.4. Jan. 9, 2013. DSM Letter accompanying subsequently filed items, 1 page.
Opposition Proceedings in European Application No. 07802604.4. Jan. 9, 2013. DSM letter enclosing document D19, 1 page.
Opposition Proceedings in European Application No. 07802604.4. Dec. 19, 2012. (Electronic) Receipt of online submission, 1 page.
Opposition Proceedings in European Application No. 07802604.4. Dec. 19, 2012. DSM letter accompanying online submission, 1 page.
Opposition Proceedings in European Application No. 07802604.4. Dec. 19, 2012. DSM letter regarding the opposition procedure (no time limit), 6 pages.
Opposition Proceedings in European Application No. 07802604.4. Oct. 31, 2012. Brief EPO communication enclosing letter from proprietor of patent of Oct. 16, 2012, 1 page.
Opposition Proceedings in European Application No. 07802604.4. Oct. 18, 2012. Authorisation of representative, 1 page.
Opposition Proceedings in European Application No. 07802604.4. Oct. 18, 2012. Letter enclosing authorisation of representative, 1 page.
Opposition Proceedings in European Application No. 07802604.4. Oct. 17, 2012. Brief EPO communication enclosing letter from proprietor of patent of Oct. 11, 2012, 1 page.
Opposition Proceedings in European Application No. 07802604.4. Oct. 11, 2012. (Electronic) Receipt of online submission, 1 page.
Opposition Proceedings in European Application No. 07802604.4. Oct. 11, 2012. Brief EPO communication enclosing letter from proprietor of patent of Sep. 27, 2012, 1 page.
Opposition Proceedings in European Application No. 07802604.4. Oct. 11, 2012. Brief EPO communication to applicant/representative enclosing EPO Form 2548 of Oct. 11, 2012, 2 pages.
Opposition Proceedings in European Application No. 07802604.4. Oct. 11, 2012. Communication concerning the filing of a power of attorney, 2 pages.
Opposition Proceedings in European Application No. 07802604.4. Oct. 11, 2012. Communication of amended entries concerning the representative, 1 page.
Opposition Proceedings in European Application No. 07802604.4. Oct. 11, 2012. Letter accompanying subsequently filed items, 1 page.
Opposition Proceedings in European Application No. 07802604.4. Oct. 11, 2012. Request for change of applicant's representative, 1 page.
Opposition Proceedings in European Application No. 07802604.4. Oct. 10, 2012. Brief EPO communicatino to applicant/representative enclosing Form 2575, 1 page.
Opposition Proceedings in European Application No. 07802604.4. Oct. 10, 2012. Communication of amended entries, appointment of representative, 1 page.
Opposition Proceedings in European Application No. 07802604.4. Oct. 9, 2012. CDS Clean up—amended data concerning the representative for the applicant, 1 page.
Opposition Proceedings in European Application No. 07802604.4. Oct. 1, 2012. Authorisation of representative, 1 page.
Opposition Proceedings in European Application No. 07802604.4. Oct. 1, 2012. Auxiliary Request 1 during Opposition procedure, 2 pages.
Opposition Proceedings in European Application No. 07802604.4. Oct. 1, 2012. Letter regarding the opposition procedure (no time limit), supplement to response to the opposition, 4 pages.
Opposition Proceedings in European Application No. 07802604.4. Oct. 1, 2012. Faxed request for change of applicant's representative, 1 page.
Opposition Proceedings in European Application No. 07802604.4. Sep. 27, 2012. Faxed authorisation of representative, 1 page.
Opposition Proceedings in European Application No. 07802604.4. Sep. 27, 2012. Cover sheet for fax transmission, 1 page.
Opposition Proceedings in European Application No. 07802604.4. Sep. 27, 2012. Faxed letter regarding the opposition procedure (no time limit), supplement to response to the opposition, 4 pages.
Opposition Proceedings in European Application No. 07802604.4. Sep. 27, 2012. Faxed Auxiliary Request 1 during Opposition procedure, 2 pages.
Opposition Proceedings in European Application No. 07802604.4. Sep. 27, 2012. Faxed request for change of applicant's representative, 1 page.
Opposition Proceedings in European Application No. 07802604.4. Sep. 26, 2012. (Electronic) Receipt of online submission, 1 page.
Opposition Proceedings in European Application No. 07802604.4. Sep. 26, 2012. Letter accompanying subsequently filed items, 1 page.
Opposition Proceedings in European Application No. 07802604.4. Sep. 26, 2012. Request for change of opponent's representative, 1 page.
Opposition Proceedings in European Application No. 07802604.4. Sep. 20, 2012. Brief EPO communication enclosing letter from opponent of Sep. 14, 2012, 1 page.
Opposition Proceedings in European Application No. 07802604.4. Sep. 14, 2012. Fax of authorisation of representative, 1 page.
Opposition Proceedings in European Application No. 07802604.4. Sep. 14, 2012. Fax of General Power of Attorney, 2 pages.
Opposition Proceedings in European Application No. 07802604.4. Sep. 14, 2012. Fax of request for change of opponent's representative, 1 page.
Opposition Proceedings in European Application No. 07802604.4. Nov. 28, 2011. Brief EPO communication enclosing letter from proprietor of patent of Nov. 23, 2011, 1 page.
Opposition Proceedings in European Application No. 07802604.4. Nov. 23, 2011. (Electronic) Receipt of online submission, 2 pages.
Opposition Proceedings in European Application No. 07802604.4. Nov. 23, 2011. Online submission in opposition proceedings, 1 page.
Opposition Proceedings in European Application No. 07802604.4. Nov. 23, 2011. Auxiliary Request during Opposition procedure, marked-up claims, 2 pages.
Opposition Proceedings in European Application No. 07802604.4. Nov. 23, 2011. Closure of the limitation/revocation proceedings, 1 page.
Opposition Proceedings in European Application No. 07802604.4. Nov. 23, 2011. Marked-up claims, Main Request during Opposition procedure, 2 pages.
Opposition Proceedings in European Application No. 07802604.4. Nov. 23, 2011. Reply of the patent proprietor to the notice(s) of opposition, 3 pages.
Opposition Proceedings in European Application No. 07802604.4. Sep. 22, 2011. Brief EPO communication enclosing EPO Form 2944C of Sep. 22, 2011 to the proprietor, 1 page.
Opposition Proceedings in European Application No. 07802604.4. Sep. 22, 2011. Grant of extension of time limit (opposition procedure), 1 page.
Opposition Proceedings in European Application No. 07802604.4. Sep. 16, 2011. (Electronic) Receipt of online submission, 1 page.
Opposition Proceedings in European Application No. 07802604.4. Sep. 16, 2011. Letter accompanying subsequently filed items, 1 page.
Opposition Proceedings in European Application No. 07802604.4. Sep. 16, 2011. Request for extension of time, 1 page.
Opposition Proceedings in European Application No. 07802604.4. May 23, 2011. Communication of a notice of opposition and request to file observations, 1 page.

(56) References Cited

OTHER PUBLICATIONS

Opposition Proceedings in European Application No. 07802604.4. May 23, 2011. Notice of further oppositions to opponent(s) pursuant to Rule 79(2) EPC, 1 page.
Opposition Proceedings in European Application No. 07802604.4. Feb. 4, 2011. CDS Clean up—amendd data concerning the representative for the opponent, 1 page.
Opposition Proceedings in European Application No. 07802604.4. Jan. 20, 2011. pronovem Office Van Malderen executed acknowledgment of delivery, 1 page.
Opposition Proceedings in European Application No. 07802604.4. Jan. 17, 2011. pronovem Office Van Malderen executed acknowledgment of delivery, 2 pages
Opposition Proceedings in European Application No. 07802604.4. Jan. 13, 2011. pronovem Office Van Malderen acknowledgement of a document, 1 page.
Opposition Proceedings in European Application No. 07802604.4. Jan. 5, 2011. Decision to terminate the limitation procedure (opposition procedure pending) pursuant to Rule 93(2) EPC, 1 page.
Opposition Proceedings in European Application No. 07802604.4. Jan. 5, 2011. Means of redress, 1 page.
Opposition Proceedings in European Application No. 07802604.4. Jan. 4, 2011. Communication of a notice of opposition—first information to patent proprietor, 1 page.
Opposition Proceedings in European Application No. 07802604.4. Dec. 22, 2010. Declaration of José Masenbroek, 1 page.
Opposition Proceedings in European Application No. 07802604.4. Dec. 22, 2010. Curriculum vitae of José Masenbroek, 1 page.
Opposition Proceedings in European Application No. 07802604.4. Dec. 22, 2010. Confirmation copies of first pages of non-patent literature cited during the opposition procedure, 29 pages.
Opposition Proceedings in European Application No. 07802604.4. Dec. 22, 2010. Letter accompanying subsequently filed items, 2 pages.
Opposition Proceedings in European Application No. 07802604.4. Dec. 22, 2010. Confirmation Notice of opposition, 38 pages.
Opposition Proceedings in European Application No. 07802604.4. Dec. 22, 2010. Confirmation payment of fees and expenses, 1 page.
Opposition Proceedings in European Application No. 07802604.4. Dec. 20, 2010. Notice of opposition, 38 pages.
Opposition Proceedings in European Application No. 07802604.4. Dec. 20, 2010. First pages of patent documents cited during the opposition procedure, 29 pages.

* cited by examiner

METHOD OF PREPARING A CAKE USING PHOSPHOLIPASE

RELATED APPLICATIONS

This application is the U.S. National Phase filing under 35 U.S.C. §371 of PCT/EP2007/058418, filed Aug. 14, 2007, entitled "Method of Preparing a Cake Using Phospholipase", which designated the United States and was published in English on Mar. 6, 2008, which claims priority under 35 U.S.C. §119(a)-(d) to European Patent Application No. 06119649.9, filed Aug. 28, 2006.

FIELD OF THE INVENTION

The present invention relates to a method of preparing a cake.

BACKGROUND OF THE INVENTION

Basic cake ingredients are usually flour, sugar, fats (from animal or vegetal origin), eggs and leaveners. Additional ingredients may be for example milk or milk fractions, flavorings or salt (in Pyler, E. J., 1988, Baking Science and Technology, Sosland Publishing, pp. 979-981). Eggs are commonly used in the preparation of various cakes. A certain amount of eggs is generally required to obtain a good cake quality, but eggs are an expensive ingredient, so it is desirable to reduce the amount of eggs and still achieve a satisfactory cake quality.

JP 63-258528A is directed to a method for producing a sponge cake by using egg liquid treated with phospholipase.

JP 10-191871A is directed to a method for producing baked confectionery by treating a mixture with phospholipase before baking.

EP 0 426 211 A1 is directed to a method of preparing a food product containing dried lysophospholipoprotein or dried lysophospholipoprotein containing material. In this invention egg yolk is treated during 4.5 hours at 54° C., the modified egg yolk is spray dried and the dried lysophospholipoprotein is added to dry cake mix, that after reconstitution with water and baking, results in a cake with an open and moist texture.

US 2003/0175383 A1 is directed to a method of preparing a flour dough, said method comprising adding to the dough components an enzyme that under dough conditions is capable of hydrolysing a glycolipid and a phospholipid, wherein said enzyme is incapable, or substantially incapable, of hydrolyzing a triglyceride and/or a 1-monoglyceride, or a composition comprising said enzyme, and mixing the dough components to obtain a dough and to improve the strength and machinability of doughs and the volume, softness and crumb structure of bread and other baked products.

US 2003/0124647 A1 is directed to a method of modifying whey protein in an aqueous solution by treating it with phospholipase. The modified whey protein shows to have improved foaming overrun and foam stability when whipped, as compared to whey protein preparation that is not treated with a phospholipase.

SUMMARY OF THE INVENTION

The inventors confirmed that the volume and properties of a cake tend to deteriorate when the amount of eggs in the cake recipe is reduced.

They found that this deterioration can be counteracted by adding a phospholipase to the cake batter, as seen by an increased cake volume and improved cake properties, including the properties (of the fresh cake and also after storage), e.g. increased cohesiveness, increased springiness, and increased elasticity.

They found that the cake quality (as measured by these parameters) can be further improved, even up to the level of the original cake, by adding a non-egg protein together with the phospholipase.

Accordingly, in a first aspect the invention provides a method of preparing a cake, said method comprising preparing a cake batter by mixing cake batter ingredients, said ingredients comprising non-phospholipase treated egg lecithin and phospholipase, and baking the cake batter to make the cake.

Accordingly, the invention provides a method of preparing a cake, comprising:

a) preparing a cake batter comprising egg yolk lecithin,
b) adding a phospholipase to the cake batter, and
c) baking the cake batter to make the cake.

The method may further comprise adding a non-egg protein to the cake batter.

In another embodiment of the present invention the phospholipase is added to the mix of dry ingredient that is further mixed with other ingredients such as liquid eggs, oil, and water to prepare the batter.

DETAILED DESCRIPTION OF THE INVENTION

Phospholipase

The phospholipase is an enzyme that catalyzes the release of fatty acyl groups from a phospholipid. It may be a phospholipase A2 (PLA2, EC 3.1.1.4) or a phospholipase A1 (EC 3.1.1.32). It may or may not have other activities such as triacylglycerol lipase (EC 3.1.1.3) and/or galactolipase (EC 3.1.1.26).

The phospholipase may be a native enzyme derived from mammalian or microbial sources.

An example of a mammalian phospholipase is pancreatic PLA2, e.g. bovine or porcine PLA2 such as the commercial product Lecitase® 10 L (porcine PLA2, product of Novozymes A/S).

Microbial phospholipases may be derived from *Fusarium*, e.g. *F. oxysporum* phospholipase A1 (WO 1998/026057), *F. venenatum* phospholipase A1 (described in WO 2004/097012 as a phospholipase A2 called FvPLA2), from *Tuber*, e.g. *T. borchii* phospholipase A2 (called TbPLA2, WO 2004/097012).

The phospholipase may also be a lipolytic enzyme variant with phospholipase activity, e.g. as described in WO 2000/032758 or WO 2003/060112.

The phospholipase may be added in an amount of 500-20,000 units (LEU) per kg of batter, e.g. 1000-10,000 units (LEU) per kg.

The phospholipase may also catalyze the release of fatty acyl groups from other lipids present in the batter, particularly wheat lipids. Thus, the phospholipase may have triacylglycerol lipase activity (EC 3.1.1.3) and/or galactolipase activity (EC 3.1.1.26).

Protein

Compared to a conventional cake recipe the amount of egg protein may be reduced and may be replaced by non-egg-protein. For example, compared to a conventional cake recipe, the amount of egg white protein may be reduced and may be replaced by non-egg protein.

Thus, the batter used in the invention may contain 0.5-3.0% by weight of egg protein, and may contain 0.1-6% (particularly 0.5-2%) by weight of non-egg protein. For example, the batter used in the invention may contain 0.5-2.5% by weight of egg white protein, and may contain 0.1-6% (particularly 0.5-2%) by weight of non-egg protein.

The non-egg protein may particularly be a water-soluble, globular protein. The non-egg protein may particularly be partially or fully purified or isolated protein, such as, a water-soluble, globular protein. The non-egg protein may be denatured, and it may be one that partially unfolds to a rod-shaped or flexible molecule under the interaction of lyso-lecithin formed by the action of the phospholipase on the egg yolk lecithin.

Protein sources with a good waterbinding, emulsifying and gelling properties in presence of lysophospholecithin are considered especially suitable Examples of non-egg proteins are wheat proteins. Further examples of non-egg proteins are casein, whey protein, wheat gluten, legume protein (e.g. from soy bean, pea or lupine).

The non-egg protein may be subjected to a limited hydrolysis, e.g. enzymatic hydrolysis to 0-6% hydrolysis. The enzymatic hydrolysis may be carried out with an amino-acid specific protease, e.g. one which is specific for Arg, Lys, Glu, Asp and/or Pro, such as the protease described in WO 91/13554.

The modification may include steps of shear treatment and acidic or alkaline pH, e.g. as described in WO2003/13266, increased temperature to denature partially or completely, protein deamidation, and separation steps including centrifugation, decanting and ultracentrifugation.

The protein (or hydrolyzed) protein may be enzymatically modified, e.g. with a cross-linking enzyme like transglutaminase or another protein modifying enzyme like protein-glutaminase. Furthermore the protein may be modified physically or chemically, e.g. through denaturation and deamidation.

Egg Yolk Lecithin

The cake batter comprises egg yolk lecithin, e.g. in the form of whole eggs, egg yolks, or egg powder.

The invention makes it possible to reduce the amount of egg material, e.g. to about half of a conventional cake. Thus, the batter may contain 0.3-1.5% by weight of egg lecithin or 5-25% (particularly 7-20, or 8-15) by weight of whole eggs.

Advantageously, the batter may contain 0.1-1.5%, such as 0.1-1.2%, or 0.1-0.9%, or 0.2-1.5%, or 0.2-1.2%, or 0.2-0.9%, or 0.3-1.5%, or 0.3-1.2%, or 0.3-0.9% by weight of egg lecithin or 5-25% (particularly 7-20, or 8-15) by weight of whole eggs.

Other Ingredients

The cake batter may comprise other conventional ingredients, typically in the following amounts (in % by weight of the batter):

Flour (untreated, heat treated, chlorinated): 15-30%
Starch (modified, native): 0-10%
Sugar: 15-25%
Emulsifier (mono and diglycerides of fatty acids, propylene glycol esters of fatty acids, lactic acid esters of mono and diglycerides of fatty acids, sodium stearoyl-2-lactylate): 0.1-1%
Baking powder (containing soda and acid or acidic salts): 0.5-1%
Hydrocolloids (Locust bean gum, guar gum, tara gum, xanthan gum, carrageenan, acacia gum, cellulose, modified cellulose, pectin): 0-1%
Vegetable fat (ex. oil, margarine, shortening, fat paste, powdered fat): 5-30%
Water: up to 100%

Butter may advantageously replace part or all of the fat.

An example of cake is a cake prepared with eggs-sugar-wheat flour-vegetable oil-starch-baking powder: sodium bicarbonate (E500ii), sodium acid pyrophosphate (E450i)-emulsifier: mono and diglycerides of fatty acids (E471), lactic acid esters of mono and diglycerides of fatty acids (E472b), sodium stearoyl-2-lactylate (E481)-hydrocolloid: xanthan gum.

Another example of cake is a cake prepared with eggs-sugar-wheat flour-starch-margarine-baking powder: sodium bicarbonate (E500ii), sodium acid pyrophosphate (E450i)-emulsifier: mono and diglycerides of fatty acids (E471)-propylene glycol esters of fatty acids (E477)-lactic acid esters of mono and diglycerides of fatty acids (E472b), sodium stearoyl-2-lactylate (E481)-hydrocolloid: carrageenan A further example of cake is a cake prepared with eggs-sugar-wheat flour-starch-margarine-baking powder: sodium bicarbonate (E500ii), sodium acid pyrophosphate (E450i)-emulsifier: mono and diglycerides of fatty acids (E471)-propylene glycol esters of fatty acids (E477)-lactic acid esters of mono and diglycerides of fatty acids (E472b)-hydrocolloid: carrageenan Assay Methods Phospholipase Activity (LEU)

Lecithin is hydrolyzed under constant pH and temperature, and the phospholipase activity is determined as the rate of titrant (0.1N NaOH) consumption during neutralization of the liberated fatty acid. The substrate is soy lecithin (L-α-Phosphotidyl-Choline), and the conditions are pH 8.00, 40.0° C., reaction time 2 min. The method is further described in DK 99/00664 (Novo Nordisk A/S, Denmark). The phospholipase from porcine pancreas has an activity of 510 LEU/mg and is taken as standard.

Texture Profile Analysis (TPA) for Determination of Cohesiveness and Springiness Two consecutive deformations of a cylindrical crumb sample ($\phi$=45 mm) performed with a cylindrical probe ($\phi$=100 mm) with a maximum deformation of 50% of the initial height of the product are performed at a deformation speed of 2 mm/s and waiting time between consecutive deformations of 3 s. Force is recorded as a function of time.

Cohesiveness is calculated as the ratio (expressed in percent) between the surface under the second deformation curve (downwards+upwards) and the surface under the first deformation curve (downwards+upwards).

Springiness is calculated as the ratio between the height of the sample after the first deformation and 3 seconds waiting time and the initial height of the product.

Penetration Test for Determination of Elasticity

Penetration of cake crumb with a cylindrical probe ($\phi=25$ mm) until a total deformation of 25% of the initial height of the sample, at a deformation speed of 2 mm/s and keeping the target deformation constant during 20 s. Force is registered as a function of time. Elasticity is the ratio (expressed in percent) between the force measured after 20 s at constant deformation to the force applied to obtain the target deformation.

EXAMPLES

Example 1: Effect of Phospholipase

Cakes were made using a typical batter cake recipe. 15-25% eggs, 20-30% flour, 0-10% starch, vegetable fat 15-20%, 20-25% sugar, 0.1-1% emulsifier (mono and diglycerides of fatty acids, propylene glycol esters of fatty acids, lactic acid esters of mono and diglycerides of fatty acids, Sodium Stearoyl-2-lactylate), baking powder 0.8% (soda and SAPP (Sodium acid PyroPhosphate)), 0-1% hydrocolloids, 0-1% protein and water to 100% were mixed for 2 minutes at speed 2 (low) and 2 minutes at speed 5 (medium) in a Hobart mixer.

Phospholipase was added directly to the dry mix, and finally eggs and oil and water were added to form the batter. A total of 1.875 kg cake batter was prepared per trial. 300 g cake batter was weighed into aluminium pans.

The cakes were baked at a temperature of 180° C. for 45 minutes. 6 cakes with a total weight of 1.66 kg were made from each batter. Afterwards the cakes were cooled and packed in a plastic bag.

Textural properties were measured on day 1 and day after baking using the method described above. Cohesiveness, springiness and elasticity as well as volume of the cakes were evaluated.

In the first example 1500 LEU/kg or 3750 LEU/kg was added to the batter where 50% of the eggs (corresponding to 7.5-12.5% by weight of the batter) were replaced by flour and water. A control was made with 100% egg (corresponding to 15-25% by weight of the batter); the volume and textural properties were taken as 100%.

The following results show the effect of phospholipase on volume and texture of cake with 50% egg reduction and a comparison between microbial phospholipases and pancreatic phospholipase (Table 1).

The results show that for 50% egg replaced by flour, the volume of the cake was only 90%, the cohesiveness on day was only 70%, and the elasticity on day 14 was 90% compared to the Control.

By the addition of TbPLA2, Lecitase 10 L, and FvPLA2 the volume of the 50% egg cakes was improved by 4-7%. 7% volume increase was achieved for 3750 LEU/kg batter Lecitase 10 L.

The cohesiveness on day 14 was improved by 12-28%. Highest increase in cohesiveness was achieved by 3750 LEU/kg batter Lecitase 10 L.

The elasticities of the resulting cakes were increased by 2-10% on day 14. Highest increase was measured for Lecitase 10 L (1500 LEU/kg batter and 3750 LEU/kg batter), FvPLA2 (3750 LEU/kg batter) and TbPLA2 (1500 LEU/kg batter).

Cake texture and cake volume were improved by all 3 phospholipases. Lecitase 10 L gave, with only 3% difference in volume, an elasticity and a cohesiveness on day 14 comparable to a Control cake with 100% egg.

Example 2: Effect of Combination of Phospholipase and Non-Egg Protein

Cakes were prepared as in Example 1, but with phospholipase (Lecitase 10 L) and various non-egg proteins.

The following results show the effect of a combination of phospholipase and non-egg protein on volume and texture of cake prepared with 50% egg reduction (Table 2). Provabis is a soy protein; the other proteins tested are all whey proteins.

The amount of protein (dry material) added in % by weight of the batter was 1.87-2.35% for soy protein (corresponding to all dry material of the replaced egg) and 0.935-1.175% for the other proteins (corresponding to 50% of the dry material of the replaced egg).

The non-egg proteins were commercial products from the following suppliers:

Foamalac, Probake M, Carbelac 80 UHG: Carberry Group, Cork, Ireland

Hiprotal 45: Borculo Domo Ingredients, The Netherlands

Lacprodan, Nutrilac BE-7602, Nutrilac BK-8310: Arla Foods Ingredients, Denmark

Provabis: Cargill N V, Belgium

Hygel 8293, Hyfoama DSN: Kerry Bio-Science, The Netherlands

TABLE 1

| Amount of egg g/kg batter | Type of enzyme | Enzyme dosage (LEU/kg batter) | Cake volume | cohesiveness Day 1 | cohesiveness Day 14 | elasticity Day 1 | elasticity Day 14 |
| --- | --- | --- | --- | --- | --- | --- | --- |
| 190 | | 0 | 100 | 100 | 100 | 100 | 100 |
| 95 | | 0 | 90 | 68 | 70 | 90 | 89 |
| 95 | Lecitase 10L | 1500 | 94 | 82 | 95 | 93 | 99 |
| 95 | Lecitase 10L | 3750 | 97 | 84 | 98 | 93 | 97 |
| 95 | TbPLA2 | 1500 | 94 | 79 | 92 | 87 | 97 |
| 95 | TbPLA2 | 3750 | 94 | 82 | 93 | 91 | 95 |
| 95 | FvPLA2 | 1500 | 94 | 75 | 82 | 90 | 91 |
| 95 | FvPLA2 | 3750 | 94 | 81 | 92 | 91 | 98 |

TABLE 2

| Amount of egg g/kg cake batter | Type of protein source | Enzyme dosage (Lecitase 10L, LEU/kg batter) | Cake volume | cohesiveness Day 1 | cohesiveness Day 14 | springiness Day 1 | springiness Day 14 | elasticity Day 1 | elasticity Day 14 |
|---|---|---|---|---|---|---|---|---|---|
| 190 |  | 0 | 100 | 100 | 100 | 100 | 100 | 100 | 100 |
| 95 |  | 0 | 85 | 69 | 68 | 74 | 81 | 91 | 86 |
| 95 |  | 3750 | 94 | 82 | 97 | 82 | 88 | 91 | 98 |
| 95 | Whey protein (Foamalac) | 3750 | 97 | 101 | 94 | 94 | 95 | 100 | 103 |
| 95 | Whey protein (Probake M) | 3750 | 103 | 94 | 102 | 93 | 94 | 99 | 105 |
| 95 | Whey protein (Carbelac 80 UHG) | 3750 | 103 | 93 | 105 | 92 | 93 | 98 | 104 |
| 95 | Na-caseinate | 3750 | 103 | 86 | 105 | 89 | 95 | 92 | 100 |
| 95 | Whey protein (Lacprodan) | 3750 | 100 | 87 | 100 | 88 | 90 | 96 | 94 |
| 95 | Whey protein (Hygel 8293) | 3750 | 107 | 89 | 103 | 87 | 88 | 95 | 101 |
| 95 | Whey protein (Hiprotal 45) | 3750 | 103 | 86 | 100 | 86 | 91 | 95 | 96 |
| 95 | Whey protein (Nutrilac BE-7602) | 3750 | 97 | 87 | 95 | 88 | 90 | 97 | 101 |
| 95 | Whey protein (Nutrilac BK-8310) | 3750 | 94 | 84 | 87 | 88 | 88 | 99 | 103 |
| 95 | Soy protein (Provabis) | 3750 | 95 | 87 | 101 | 91 | 93 | 95 | 98 |

The results (Table 2) show that by replacing 50% of the eggs and adding a non-egg protein together and a phospholipase it was possible to reach the same cake volume and/or the same level of cohesiveness and/or elasticity after 14 days as the control.

50% egg replaced by flour resulted in a volume loss of 15% compared to the Control.

By the addition of Lecitase 10 L the volume was increased again by 9%. With some of the non-egg proteins the volume of the 50% egg cake was improved to above the volume of the Control cake, while other proteins also showed an increase of the volume, but not up to the level of the control.

Cohesiveness and elasticity were generally comparable or even above the values measured for the Control.

Springiness was improved by the non-egg proteins, but remained below the values measured for the Control on day 14.

Thus, the addition of non-egg protein together with a phospholipase can improve the volume, elasticity and cohesiveness of a 50% egg cake and make it comparable to the Control.

Example 3: Effect of Combination of Phospholipase and Non-Egg Protein

Cakes were prepared as in Example 1, but with addition of phospholipase and non-egg protein, alone or in combination (Table 3).

TABLE 3

| Amount of egg g/kg batter | Type of protein cake source | Enzyme dosage (Lecitase 10L, LEU/kg batter) | Cake volume | cohesiveness Day 1 | cohesiveness Day 14 | springiness Day 1 | springiness Day 14 | elasticity Day 1 | elasticity Day 14 |
|---|---|---|---|---|---|---|---|---|---|
| 190 |  | 0 | 100 | 100 | 100 | 100 | 100 | 100 | 100 |
| 95 |  | 0 | 91 | 69 | 68 | 78 | 83 | 90 | 87 |
| 95 |  | 3750 | 100 | 82 | 94 | 80 | 88 | 89 | 95 |
| 95 | Whey protein (Hiprotal 45) | 0 | 91 | 74 | 77 | 83 | 89 | 91 | 86 |
| 95 | Whey protein (Hiprotal 45) | 3750 | 103 | 86 | 100 | 86 | 91 | 95 | 97 |
| 95 | Whey protein (Carbelac 80UHG) | 0 | 94 | 86 | 87 | 94 | 93 | 94 | 90 |
| 95 | Whey protein (Carbelac 80UHG) | 3750 | 103 | 92 | 107 | 92 | 92 | 96 | 104 |
| 95 | Whey protein (Foamalac) | 0 | 94 | 86 | 86 | 95 | 93 | 94 | 93 |
| 95 | Whey protein (Foamalac) | 3750 | 103 | 96 | 106 | 96 | 95 | 97 | 101 |

The effect of the non-egg protein is illustrated in the data where the addition of non-egg protein alone and in combination with phospholipase is compared to 50% egg where egg has been replaced by flour and to 100% egg cakes (=Control).

It can be clearly seen that the addition of non-egg protein alone only gives slight improvement on the volume, while when combined with the Lecitase 10 L the volume is superior to the Control.

Here also the cohesiveness and the elasticity were comparable or above the values measured for the Control on day 14.

Springiness remains below the control on day 14.

Example 4: Effect of Combination of Phospholipase and Non-Egg Protein: Wheat Protein Cakes were prepared as in Example 1, but with phospholipase (Lecitase 10 L) and various non-egg proteins, i.e. wheat proteins (Tables 4a to 4d). A substantial amount of wheat proteins have been added such that the quantity of wheat protein is increased by at least 30% compared to the quantity originally present in the flour.

The following results show the effect of a combination of phospholipase and non-egg protein on volume and texture of cake prepared with 50% egg reduction.

The amount of protein (dry material) added in % by weight of the batter was 0.9067% and 1.813% (corresponding to respectively 50% and 100% of the dry material of the replaced egg).

The non-egg proteins were commercial products from the following suppliers:

Prolite 100 and Prolite 200, ADM Speciality Food Ingredients, Keokuk, USA
Meripro 420, Tate & Lyle Europe N.V., Belgium
Gemtec 2170, Manildra Group, Auburn, Australia
HWG 2009, Loryma, Zwingenberg, Germany
Arise 5000, Midwest Grain Proteins, Atchison, Kans., USA
Amygluten 110, Tate & Lyle Europe N.V., Belgium
Super Gluten 75 and Super Gluten 80, ADM
Glutastar EC75 and Glutastar EC80, Fiske Food Ingredients TABLE 4a

| Amount of egg g/kg cake batter | Type of wheat protein | Amount of wheat protein g/kg batter | Enzyme dosage (Lecitase 10L, LEU/kg batter) | Cake volume | cohesiveness Day 1 | cohesiveness Day 14 | springiness Day 1 | springiness Day 14 | elasticity Day 1 | elasticity Day 14 |
|---|---|---|---|---|---|---|---|---|---|---|
| 190 | | | | 100 | 100 | 100 | 100 | 100 | 100 | 100 |
| 95 | | | | 88 | 73 | 70 | 74 | 74 | 90 | 91 |
| 95 | | | 3750 | 97 | 87 | 96 | 78 | 82 | 92 | 101 |
| 95 | Prolite 100 | 9 | 3750 | 97 | 95 | 102 | 84 | 88 | 92 | 104 |
| 95 | Prolite 100 | 18 | 3750 | 100 | 98 | 110 | 88 | 92 | 94 | 103 |
| 95 | Prolite 200 | 9 | 3750 | 100 | 92 | 102 | 83 | 87 | 94 | 103 |
| 95 | Prolite 200 | 18 | 3750 | 100 | 100 | 109 | 88 | 91 | 96 | 107 |
| 95 | Meripro 420 | 9 | 3750 | 97 | 90 | 98 | 81 | 86 | 91 | 103 |

TABLE 4b

| Amount of egg g/kg cake batter | Type of wheat protein | Amount of wheat protein g/kg batter | Enzyme dosage (Lecitase 10L, LEU/kg batter) | Cake volume | cohesiveness Day 1 | cohesiveness Day 14 | springiness Day 1 | springiness Day 14 | elasticity Day 1 | elasticity Day 14 |
|---|---|---|---|---|---|---|---|---|---|---|
| 190 | | | | 100 | 100 | 100 | 100 | 100 | 100 | 100 |
| 95 | | | | 90 | 69 | 63 | 77 | 74 | 91 | 90 |
| 95 | | | 3750 | 97 | 81 | 96 | 81 | 87 | 91 | 96 |
| 95 | Meripro 420 | 9 | | 93 | 80 | 75 | 87 | 86 | 92 | 91 |
| 95 | Meripro 420 | 9 | 3750 | 100 | 89 | 101 | 85 | 89 | 94 | 98 |
| 95 | Meripro 420 | 18 | | 93 | 87 | 85 | 91 | 90 | 95 | 98 |
| 95 | Meripro 420 | 18 | 3750 | 100 | 91 | 107 | 90 | 92 | 97 | 99 |

TABLE 4c

| Amount of egg g/kg cake batter | Type of wheat protein | Amount of wheat protein g/kg batter | Enzyme dosage (Lecitase 10L, LEU/kg batter) | Cake volume | cohesiveness Day 1 | cohesiveness Day 14 | springiness Day 1 | springiness Day 14 | elasticity Day 1 | elasticity Day 14 |
|---|---|---|---|---|---|---|---|---|---|---|
| 190 | | | | 100 | 100 | 100 | 100 | 100 | 100 | 100 |
| 95 | | | | 85 | 73 | 70 | 74 | 74 | 90 | 91 |
| 95 | | | 3750 | 94 | 87 | 96 | 78 | 82 | 92 | 101 |
| 95 | HWG 2009 | 9 | | 87 | 64 | 63 | 68 | 75 | 90 | 87 |
| 95 | HWG 2009 | 9 | 3750 | 99 | 81 | 92 | 72 | 79 | 93 | 94 |
| 95 | HWG 2009 | 18 | | 87 | 64 | 61 | 66 | 73 | 90 | 90 |
| 95 | HWG 2009 | 18 | 3750 | 97 | 83 | 95 | 73 | 82 | 92 | 93 |
| 95 | Gemtec 2170 | 9 | | 85 | 69 | 71 | 75 | 76 | 88 | 94 |
| 95 | Gemtec 2170 | 9 | 3750 | 93 | 79 | 98 | 73 | 81 | 90 | 101 |
| 95 | Gemtec 2170 | 18 | | 90 | 77 | 75 | 83 | 81 | 89 | 94 |
| 95 | Gemtec 2170 | 18 | 3750 | 93 | 89 | 103 | 86 | 86 | 95 | 101 |
| 95 | Arise 5000 | 9 | | 90 | 72 | 73 | 74 | 79 | 91 | 89 |
| 95 | Arise 5000 | 9 | 3750 | 101 | 90 | 100 | 77 | 85 | 94 | 98 |
| 95 | Arise 5000 | 18 | | 92 | 82 | 79 | 81 | 85 | 92 | 92 |
| 95 | Arise 5000 | 18 | 3750 | 100 | 95 | 107 | 87 | 91 | 97 | 98 |

TABLE 4d

| Amount of egg g/kg cake batter | Type of wheat protein | Amount of wheat protein g/kg batter | Enzyme dosage (Lecitase 10L, LEU/kg batter) | Cake volume | cohesiveness Day 1 | cohesiveness Day 7 | springiness Day 1 | springiness Day 7 | elasticity Day 1 | elasticity Day 7 |
|---|---|---|---|---|---|---|---|---|---|---|
| 190 | | | | 100 | 100 | 100 | 100 | 100 | 100 | 100 |
| 95 | | | | 90 | 81 | 85 | 90 | 87 | 66 | 78 |
| 95 | | | 2667 | 100 | 86 | 91 | 88 | 88 | 72 | 82 |
| 95 | Super Gluten 75 | 9 | 2667 | 102 | 85 | 98 | 87 | 85 | 70 | 89 |
| 95 | Super Gluten 80 | 9 | 2667 | 101 | 86 | 98 | 86 | 86 | 71 | 88 |
| 95 | Meripro 420 | 9 | 2667 | 99 | 88 | 98 | 89 | 87 | 76 | 90 |
| 95 | Glutastar EC75 | 9 | 2667 | 98 | 88 | 100 | 87 | 85 | 74 | 91 |
| 95 | Glutastar EC80 | 9 | 2667 | 99 | 89 | 100 | 87 | 84 | 75 | 91 |

The effect of the non-egg protein(s) is illustrated in the data presented on the tables 4a to 4d where the addition of non-egg protein(s) alone or in combination with phospholipase is compared to 50% egg formulations where egg has been replaced by flour and to 100% egg cakes (=Control).

Table 4a. When combining wheat protein and phospholipase (Lecitase 10 L) in cake prepared with 50% less egg, volume of cake prepared with 100% egg can be completely recovered. When adding Prolite 100 or Prolite 200 in combination with phospholipase to 50% egg formulations cohesiveness and elasticity of crumb 14 days after baking can be recovered or even increased and springiness is improved.

Table 4b. Meripro 420, when added alone, has only a slight positive effect on volume of cake prepared with 50% less egg. Volume of cake prepared with 100% egg can be completely recovered by adding a combination of phospholipase and Meripro 420 to a 50% egg formulation. Cohesiveness is highly improved when adding both phospholipase and Meripro 420.

Table 4c. Wheat proteins tested, when added alone, have only a slight positive effect on volume. HWG2009 has a positive effect on volume but not on texture properties of cake prepared with 50% egg and phospholipase. Gemtec 2170 has no effect on volume of cake prepared with 50% egg and phospholipase but a positive effect on cohesiveness 14 days after baking and springiness 1 and 14 days after baking. Arise 5000 in combination with phospholipase has a positive effect on volume and cohesiveness of 50% egg cake.

Table 4d. When adding wheat proteins: Meripro 420, Super Gluten 75, Super Gluten 80, Glutastar EC75 or Glutastar EC80 to a 50% egg cake recipe containing Lecitase 10 L, cohesiveness and resiliency measured 7 days after baking are significantly increased (between 7 and 9%) when comparing these parameters measured 7 days after baking on 50% egg cake only containing Lecitase 10 L.

Example 5: Effect of Combination of Phospholipase and Non-Egg Proteins: Sensorial Analysis Cakes were prepared as in Example 1, but without hydrocolloids and with phospholipase (Lecitase 10 L) and two different non-egg proteins: Prolite 100 (ADM Speciality Food Ingredients, Keokuk, USA) and Meripro 420 (Tate & Lyle Europe N.V., Aalst, Belgium).

Five different cake samples have been subjected to sensorial analysis by 29 subjects.
1. reference cake with 100% egg.
2. reference cake with 50% egg and replacement of egg by flour and water.
3. reference cake with 50% egg and replacement of egg by 3750 LEU lecitase 10 L/kg batter+9 g/kg batter Meripro 420+9 g/kg batter of flour+water.
4. reference cake with 50% egg and replacement of egg by 3750 LEU lecitase 10 L/kg batter+9 g/kg batter Prolite 100+9 g/kg batter of flour+water.
5. reference cake with 50% egg and replacement of egg by 3750 LEU lecitase 10 L/kg batter+18 g/kg batter Meripro 420.

Subjects have been asked to rank the different cakes according to their preference with the highest value for the highest appreciated cake and the lowest value for the less appreciated cake (Table 5).

TABLE 5

| | Cake | Sum of rankings |
|---|---|---|
| 1 | Reference 100% egg | 90.0 |
| 2 | Reference 50% egg | 64.5 |
| 2 | 50% egg + lecitase + 9 g Meripro 420/kg batter | 91.0 |
| 4 | 50% egg + lecitase + 9 g Prolite 100/kg batter | 96.0 |
| 5 | 50% egg + lecitase + 18 g Meripro 420/kg batter | 93.5 |

The sum of rankings indicates that cake prepared with only 50% egg is less appreciated and that the four other types of cake are equally appreciated.

Example 6: Effect of Combination of Phospholipase and Non-Egg Protein: Different Types of Cakes Cakes were prepared with two different types of commercial dry mixes from Puratos (Brussels, Belgium): Tegral Satin Cream Cake and Tegral Allegro Cake and with phospholipase (Lecitase 10 L) and Meripro 420 (Tate & Lyle Europe N.V., Aalst, Belgium). The margarine added is Aristo Cake (Puratos, Brussels, Belgium). The oil added is rapeseed oil. Batter is prepared and cakes are baked as described in example 1. The regular composition of the batters is given in table 6.

TABLE 6

| | Regular Batter composition | | | |
|---|---|---|---|---|
| Type of dry mix | Dry mix (g) | Liquid pasteurized egg (g) | Fat (g) | Water (g) |
| Tegral Satin Cream Cake | 1000 | 350 | 300 rapeseed oil | 225 |
| Tegral Allegro Cake | 1000 | 500 | 500 margarine | 0 |

The following results show the effect of a combination of phospholipase and non-egg protein(s) on volume and texture of cake prepared with 50% egg reduction (Table 7).

TABLE 7

| Amount of egg g/kg cake batter | Type of cake | Amount of Meripro 420 g/kg batter | Enzyme dosage (Lecitase 10L, LEU/kg batter) | Cake volume | cohesiveness Day 1 | cohesiveness Day 14 | springiness Day 1 | springiness Day 14 | elasticity Day 1 | elasticity Day 14 |
|---|---|---|---|---|---|---|---|---|---|---|
| 190 | Tegral Satin Cream Cake | | | 100 | 100 | 100 | 100 | 100 | 100 | 100 |
| 95 | Tegral Satin Cream Cake | | | 88 | 73 | 70 | 74 | 74 | 90 | 91 |
| 95 | Tegral Satin Cream Cake | 9 | 3750 | 97 | 89 | 101 | 85 | 89 | 94 | 98 |
| 250 | Tegral Allegro Cake | | | 100 | 100 | 100 | 100 | 100 | 100 | 100 |
| 125 | Tegral Allegro Cake | | | 80 | 65 | 63 | 78 | 82 | 93 | 92 |

TABLE 7-continued

| Amount of egg g/kg cake batter | Type of cake | Amount of Meripro 420 g/kg batter | Enzyme dosage (Lecitase 10L, LEU/ kg batter) | Cake volume | cohesiveness Day 1 | cohesiveness Day 14 | springiness Day 1 | springiness Day 14 | elasticity Day 1 | elasticity Day 14 |
|---|---|---|---|---|---|---|---|---|---|---|
| 125 | Tegral Allegro Cake | 12.5 | 3500 | 85 | 94 | 123 | 93 | 100 | 95 | 91 |

Cake volume and texture were improved in recipe with 50% egg reduction by the use of a combination of non-egg protein(s) and phospholipase.

The invention claimed is:

1. A method for preparing a cake, comprising preparing a cake batter by mixing cake batter ingredients, and baking the cake batter to make the cake, wherein said cake batter ingredients comprise a phospholipase and eggs wherein the said eggs comprise egg yolk lecithin in an amount to provide between 0.2% and 0.4% of the said egg yolk lecithin in the said batter.

2. The method of claim 1 wherein the phospholipase is a phospholipase A2.

3. The method of claim 1, wherein the phospholipase is added in an amount of 500-20000 LEU per kg cake batter.

4. The method of claim 1, wherein said eggs in said cake batter comprise whole eggs in an amount of 8-15% by weight of the cake batter.

5. The method of claim 1, wherein a non-egg protein is added to the cake batter.

6. The method of claim 5 wherein the non-egg protein is selected from the group consisting of whey protein, wheat protein and soy protein.

7. The method of claim 5 where the protein is a modified protein.

8. The method of claim 5, wherein the non-egg protein is in an amount of 0.1-6% by weight of cake batter.

9. The method of claim 1, wherein the cake batter further comprises an emulsifier.

10. The method of claim 9, wherein the emulsifier is in an amount of 0.1-1% of the cake batter.

11. The method of claim 1, wherein the cake batter further comprises flour, sugar, vegetable fat and an emulsifier.

12. The method of claim 11, wherein the flour is in an amount of 15-30% by weight, the sugar is in an amount of 15-25% by weight, the vegetable fat is in an amount of 5-30% by weight, and the emulsifier is in an amount of 0.1-1% by weight of cake batter.

13. The method of claim 1, wherein said phospholipase is a mammalian pancreatic phospholipase.

14. The method of claim 1, wherein the egg is whole egg.

15. The method of claim 1, wherein the egg is liquid egg.

16. A method according to claim 1, wherein said cake batter ingredients comprise eggs in an amount of 7.5 to 12.5% by weight of the batter.

17. A cake prepared according to the method of any one of claim 1, 2, 3, 4, 5, 6, 7, 9, 11, 13, 8, 10 or 12.

18. A method for preparing a cake, comprising preparing a cake batter by mixing cake batter ingredients, and baking the cake batter to make the cake, wherein said cake batter ingredients comprise a phospholipase and whole liquid eggs in an amount of 8-15% by weight of the cake batter, wherein the said cake batter ingredients further comprise flour in an amount of 15-30% by weight, sugar in an amount of 15-25% by weight, vegetable fat in an amount of 5-30% by weight, and emulsifier is in an amount of 0.1-1% by weight of batter.

19. A method for preparing a cake, comprising preparing a cake batter by mixing cake batter ingredients, and baking the cake batter to make the cake, wherein said cake batter ingredients comprise a phospholipase and eggs in an amount of 7.5-12.5% by weight of the batter, wherein the said eggs comprise egg yolk lecithin in an amount to provide between 0.2% and 0.4% of the said egg yolk lecithin in the said batter, wherein the cake thus obtained has a reduced amount of egg but has comparable volume, and/or comparable cohesiveness and/or comparable springiness than a cake obtained by baking a batter comprising typical cake recipe of 15-25% whole liquid eggs, 20-30% flour, 15-20% vegetable fat and/or butter, and 20-25% sugar.

* * * * *